(12) United States Patent
Shah

(10) Patent No.: US 8,795,595 B2
(45) Date of Patent: Aug. 5, 2014

(54) SENSOR SUBSTRATE SYSTEMS AND METHODS

(75) Inventor: Rajiv Shah, Rancho Palos Verdes, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 704 days.

(21) Appl. No.: 12/772,050

(22) Filed: Apr. 30, 2010

(65) Prior Publication Data

US 2011/0248184 A1    Oct. 13, 2011

Related U.S. Application Data

(60) Provisional application No. 61/321,614, filed on Apr. 7, 2010.

(51) Int. Cl.
   *G01N 21/64*      (2006.01)
   *G01N 33/48*      (2006.01)
   *G01N 33/66*      (2006.01)

(52) U.S. Cl.
   USPC ............ 422/82.07; 436/164; 436/91; 436/95; 436/172; 422/401; 422/68.1; 422/82.05; 422/82.08; 600/322; 600/342; 600/365

(58) Field of Classification Search
   USPC ............... 422/401, 68.1, 82.05, 82.07, 82.08; 436/164, 172, 91, 95; 600/322, 342, 600/347, 365
   See application file for complete search history.

(56) References Cited

U.S. PATENT DOCUMENTS

| | | | |
|---|---|---|---|
| 6,671,527 | B2 | 12/2003 | Petersson et al. |
| 6,994,691 | B2 | 2/2006 | Ejlersen |
| 7,138,330 | B2 | 11/2006 | Shah et al. |
| 7,228,159 | B2 | 6/2007 | Petersson et al. |
| 7,297,627 | B2 | 11/2007 | Shah et al. |
| 7,323,142 | B2 * | 1/2008 | Pendo et al. ............... 422/82.01 |
| 7,514,038 | B2 | 4/2009 | Pendo et al. |
| 7,541,598 | B2 | 6/2009 | Aasmul |
| 7,781,328 | B2 | 8/2010 | Shah et al. |
| 8,003,513 | B2 | 8/2011 | Shah et al. |
| 2003/0049166 | A1 | 3/2003 | Pendo et al. |
| 2004/0061232 | A1 | 4/2004 | Shah et al. |
| 2005/0090866 | A1 | 4/2005 | Miller et al. |
| 2005/0148832 | A1 | 7/2005 | Reghabi et al. |
| 2008/0050281 | A1 | 2/2008 | Pendo et al. |
| 2008/0125838 | A1 * | 5/2008 | Francis .......................... 607/92 |
| 2009/0098643 | A1 | 4/2009 | Mastrototaro et al. |
| 2009/0131773 | A1 | 5/2009 | Struve et al. |

OTHER PUBLICATIONS

PCT International Search Report and Written Opinion for PCT/US2011/031286.

* cited by examiner

*Primary Examiner* — Lyle Alexander
(74) *Attorney, Agent, or Firm* — Pillsbury Winthrop Shaw Pittman LLP

(57) ABSTRACT

A sensing apparatus may include a substrate having a first side for a sensing element and a second side for electronics, the substrate may have a at least one via from the first side of the substrate to the second side of the substrate, the at least one via may be hermetically sealed with an optically transmissive material.

27 Claims, 21 Drawing Sheets

SENSOR SUBSTRATE SYSTEMS AND METHODS

CROSS-REFERENCE TO RELATED PATENT APPLICATIONS

This application claims priority from Provisional Application U.S. Application 61/321,614, filed Apr. 7, 2010, incorporated herein by reference in its entirety.

BACKGROUND

1. Field of the Invention

Embodiments of the present invention generally relate to sensor technology, and, in specific embodiments, to hermetically sealed substrates used for sensing a variety of parameters, including physiological parameters.

2. Related Art

The combination of biosensors and microelectronics has resulted in the availability of portable diagnostic medical equipment that has improved the quality of life for countless people. Many people suffering from disease or disability who, in the past, were forced to make routine visits to a hospital or doctor's office for diagnostic testing currently perform diagnostic testing on themselves in the comfort of their own homes using equipment with accuracy to rival laboratory equipment.

Nonetheless, challenges in the biosensing field have remained. For example, although many diabetics currently utilize diagnostic medical equipment in the comfort of their own homes, the vast majority of such devices still require diabetics to draw their own blood and inject their own insulin. Drawing blood typically requires pricking a finger. For someone who is diagnosed with diabetes at an early age, the number of self-induced finger pricks over the course of a lifetime could easily reach into the tens of thousands. In addition, the number of insulin injections may also reach into tens of thousands. Under any circumstances, drawing blood and injecting insulin thousands of times is invasive and inconvenient at best and most likely painful and emotionally debilitating.

Some medical conditions have been amenable to automated, implantable sensing. For example, thousands of people with heart conditions have had pacemakers or defibrillators implanted into their bodies that utilize sensors for monitoring the oxygen content of their blood. Ideally, these sensors should be able to determine whether, for example, a person's heart is running very efficiently at a high heart rate or whether a person's heart has entered defibrillation. In order to make this determination effectively, an accurate sensor must be employed. Unfortunately, oxygen sensors implanted into the body, thus far, have typically required frequent and periodic checking and recalibration. In fact, one of the "holy grails" of the pacemaker industry has been an accurate, no drift, no calibration oxygen sensor. Until recently, such a sensor has been unavailable.

An ideal solution to the diagnostic requirements of those with disease or disability, absent an outright cure, is a sensor system that may be implanted into the body and that may remain in the body for extended periods of time without the need to reset or recalibrate the sensor. Regardless of the particular application for such a sensor system, in order to affect such a system the associated sensor must remain accurate, exhibit low drift and require no recalibration for extended periods. Such a system would typically require a sensor to be located in close proximity to sensing electronics in order to maintain the required characteristics.

However, attempts to place sensor electronics in close proximity to the sensor in implantable sensor systems have historically suffered from the environment in which they operate. For example, in an implantable sensor system for diabetics, a sensor is needed to detect an amount of glucose in the blood. Consequently, the sensor must be implanted within the body in such a manner that it comes into direct contact with the blood. However, in order to place the sensor electronics in such a system in close proximity to the sensor, the sensor electronics themselves must be placed into the blood as well. This poses obvious dangers for the sensor electronics. The sensor electronics must remain in electrical contact with the sensor; however, any exposure of the sensor electronics to the blood or any other fluid would potentially short circuit the sensor electronics and destroy the entire system.

Thus, an ideal implantable sensor system would provide for a sensor to be in close proximity to sensor electronics while also providing hermeticity between the sensor, which may be exposed to fluids, and the sensor electronics, which must remain free from short circuiting fluids. In addition, the required hermeticity must be maintained over the life of the sensing system. The present invention provides such a system.

SUMMARY OF THE DISCLOSURE

A sensing apparatus may include a substrate having a first side for a sensing element and a second side for electronics. The substrate may have at least one via from the first side of the substrate to the second side of the substrate. The at least one via may be hermetically sealed from the first side of the substrate to the second side of the substrate. The at least one via may be at least partially filled with an optically transmissive material.

In various embodiments, the optically transmissive material may comprise a fritted glass material. In some embodiments, the fitted glass material may comprise at least one of quartz and silica.

In various embodiments, the at least one via may be at least partially filled with an electrically conductive material. In some embodiments, the optically transmissive material may be concentrically arranged with respect to the electrically conductive material. In some embodiments, the electrically conductive material may comprise a fritless ink. In some embodiments, the electrically conductive material may comprise an indium tin oxide.

In various embodiments, substrate may be made of a material comprising ceramic. In various embodiments, the at least one via may comprise a plurality of vias. In some embodiments, at least one of the plurality of vias may be at least partially filled with an optically transmissive material. At least one other of the plurality of vias may be at least partially filled with an electrically conductive material.

In various embodiments, the substrate may be annealed. In various embodiments, the at least one via may be filled with the optically transmissive material is polished.

In various embodiments, the sensing apparatus may include the sensing element. The sensing element may be for sensing an analyte. In some embodiments, the sensing element may be for sensing a fluorescence resonance energy transfer of the analyte. In some embodiments, the sensing apparatus may include the electronics. The electronics may comprise an illumination device for illuminating the analyte.

In further embodiments, the illumination device may comprise at least one of a light emitting device, a vertical cavity surface emitting laser, and an edge emitting laser. In further embodiments, the illumination device may be arranged to illuminate the analyte through the at least one via in the substrate. In further embodiments, the electronics may include a sensor for measuring a returned fluorescence from the sensing element. In yet further embodiments, the sensor may be arranged to sense the returned fluorescence from the sensing element through the at least one via in the substrate.

A method of manufacturing a sensing apparatus may include, but is not limited to, any one of or combination of: (i) providing a substrate having a first side for a sensing element and a second side for electronics; (ii) forming at least one via from the first side of the substrate to the second side of the substrate; and (iii) filling the at least one via at least partially with an optically transmissive material such that the at least one via is hermetically sealed from the first side of the substrate to the second side of the substrate.

In various embodiments, the method may include, but is not limited to, any one of or combination of: (iv) arranging at least one of optical emitting device and a receiving device on the second side of the substrate to pass light through the at least one via to the first side of the substrate; and (v) arranging an optically detectable material that is reactive in an optically detectable manner on the first side of the substrate to receive light from the optical emitting device and is optically detectable through the at least one via by the receiving device.

DETAILED DESCRIPTION

Figure 1:
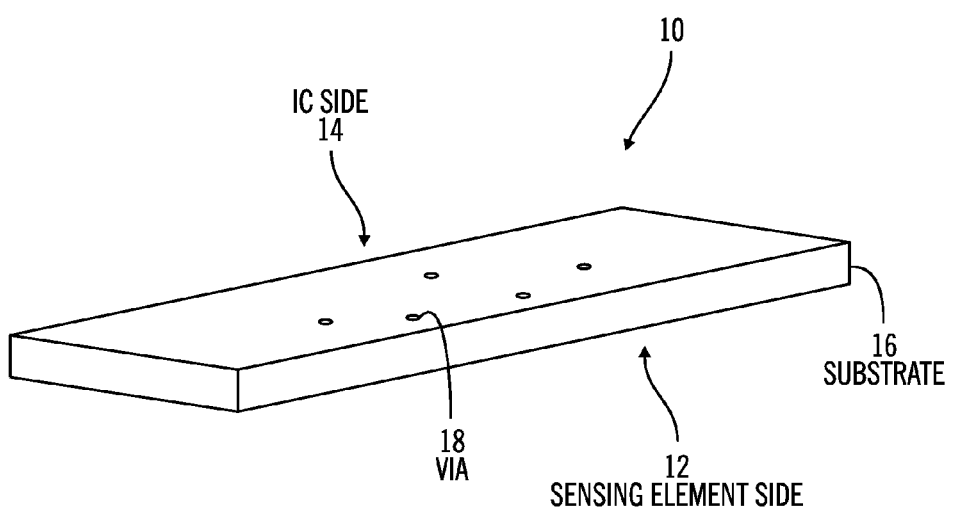
FIG. 1 is a perspective view of a generalized substrate configuration according to an embodiment of the present invention.

FIG. 1 shows a generalized substrate configuration according to an embodiment of the present invention. In various embodiments, the substrate as discussed throughout the disclosure may be employed in a sensor system as will be discussed in detail. In other embodiments, the substrate may be employed in catheters, subcutaneous implants, vascular implants, external sensors, and/or the like. A sensor 10 may have a sensing element side 12 of a substrate 16 on which a biosensing element, physiological parameter sensing element or other sensing element may be affixed. The sensor 10 may have an electronics side 14 of the substrate 16 on which electronics may be affixed for processing signals generated by the sensing element. The sensor 10 (and/or components thereof) and/or the processes for producing such a sensor (and/or components thereof) are discussed throughout this disclosure.

Other examples of the sensor 10 (and/or components thereof) and/or the processes for producing such a sensor (and/or components thereof) may be found in the following U.S. patent applications that were assigned to the assignee of the present invention, where each of following patent applications is incorporated herein by reference in its entirety: (i) U.S. patent application Ser. No. 10/331,186, filed Dec. 26, 2002; (ii) U.S. patent application Ser. No. 10/671,996, filed Sep. 26, 2003; (iii) U.S. patent application Ser. No. 10/845,002, filed May 12, 2004; (iv) U.S. patent application Ser. No. 11/086,936,186, filed Mar. 22, 2005; (v) U.S. patent application Ser. No. 11/868,898, filed Oct. 8, 2007; (vi) U.S. patent application Ser. No. 12/271,134, filed Nov. 14, 2008; (vii) U.S. patent application Ser. No. 10/038,276, filed Jan. 2, 2002; (viii) U.S. patent application Ser. No. 10/861,976, filed Jun. 4, 2004; (ix) U.S. patent application Ser. No. 10/996,026, filed Nov. 22, 2004; (x) U.S. patent application Ser. No. 11/924,402, filed Oct. 25, 2007; (xi) U.S. Patent Provisional Application Ser. No. 60/414,289, filed Sep. 27, 2002; and (xii) U.S. Patent Provisional Application Ser. No. 60/318, 055, filed Sep. 7, 2001.

The sensing element side 12 may support any of a variety of sensing elements. For example, the sensing element may be a glucose sensor utilizing a glucose oxidase enzyme as a catalyst. Alternatively, the sensing element may be an oxygen sensor or may include a plurality of sensing elements. In various embodiments, the sensing element may be a sensor for sensing cholesterol, glutamate, alcohol, lactate, or any other molecules that have an oxidase-based enzyme. In various embodiments, the sensing element may be a sensor for sensing a redox reaction and/or the like.

The electronics side 14 may support a variety of electronic circuits. According to one embodiment of the invention, the electronics side 14 of the substrate 16 may support an application specific integrated circuit (ASIC) containing data acquisition circuitry. Thus, analog signals received from the sensing element on the sensing element side 12 of the substrate 16 may be digitized by the ASIC on the electronics side 14 of the substrate 16. By positioning digitizing and other electronics close to the source of the analog signals and avoiding long cables along which signals are typically sent to be digitized, noise levels, offsets, and signal loss may be reduced. As a result, accuracy and reliability of the device may be increased. In addition, once the signals have been digitized by the electronics on the electronics side 14 of the substrate 16, the digitized signals may be sent to other devices for operation or other processing in discrete form rather than analog form, which may result in improved leakage, drift, and other characteristics.

Figure 2A:
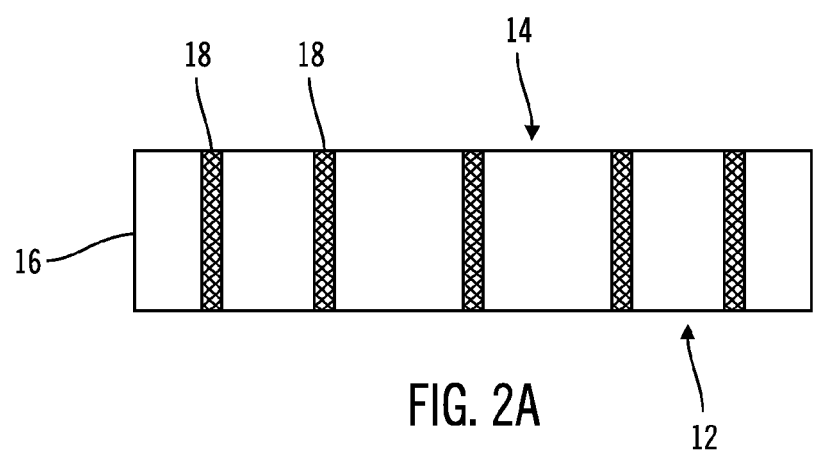
FIG. 2A is a cut-away view of vias extending through a substrate according to an embodiment of the present invention.

One or more vias 18 may extend from the sensing element side 12 of the substrate 16 to the electronics side 14 of the substrate 16. As shown in FIG. 2A, the vias 18 are pathways through the body of the substrate 16 that allow for communication (e.g., electrical contact) between an array of electrodes or other electrical contacts reacting with the sensing element on the sensing element side 12 of the substrate 16 and electronics on the electronics side 14 of the substrate 16.

Figure 2B:
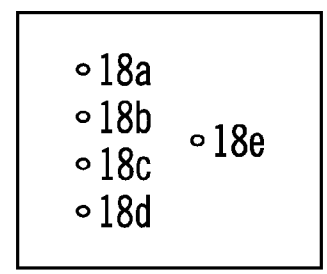
FIG. 2B is a top view of a via arrangement on a substrate according to an embodiment of the present invention.

The vias 18 may be arranged in a variety of fashions. A via arrangement for one sensing element according to one embodiment of the present invention may be seen in FIG. 2B. The via arrangement shown in FIG. 2B may correspond to electrodes that interact with an enzyme used as a catalyst in the sensing element. A first via 18a and a second via 18b may correspond to a first working electrode and a first counter electrode. A third via 18c and a fourth via 18d may correspond to a second working electrode and a second counter electrode. A fifth via 18e may correspond to a reference electrode. Electrodes may be arranged to line up with the vias 18, for example, using one of the processes described throughout this disclosure.

In various embodiments, the generalized substrate configuration of electronics adjacent to a sensing element on opposite sides of the substrate 16 (FIG. 1) and the resulting ability to output discrete signals rather than analog signals from the sensor results in a stable device. Sensor electrode output drift of less than 5% over periods of one year or more may be possible using such embodiments. With such a low drift specification, replacement or calibration intervals may be greatly reduced, allowing such embodiments to be implanted into a human body for extended periods.

The generalized substrate configuration shown in FIG. 1 benefits from processes according to embodiments of the present invention, to be described below, that result in hermeticity between the sensing element side 12 of the substrate 16 and the electronics side 14 of the substrate 16. In various embodiments, hermeticities corresponding to a helium leak rate of $1\times10^{-8}$ cc/sec at 1 atmosphere over a three-year period may be obtained.

In addition, in various embodiments, the sensor 10 may be implanted into the human body, for example, residing in a vein or artery. In addition, the sensing element side 12 of the substrate 16 may be exposed to fluids, such as, for example, blood. In this type of use, should the fluids infiltrate the electronics on the electronics side 14 of the substrate 16, the fluids would destroy the electronics and render the device useless. However, because the electronics side 14 of the substrate 16 may be hermetically sealed from the sensing element side 12 of the substrate as discussed throughout this disclosure, electronics may be placed directly on the electronics side 14 of the substrate 16 without exposure to fluids or other elements encountered by the sensing element that may damage the electronics.

The substrate 16 may be fabricated from a variety of materials. According to one embodiment of the present invention, the substrate 16 may be fabricated from ceramic. For example, the substrate 16 may be fabricated using a pressed ceramic slurry in tape form, which is widely available commercially. Also according to one embodiment of the invention, a substrate of 92%-96% alumina ($Al_2O_3$) may be used. The substrate material may be bought in sheet form, which may be flexible or rigid.

The substrate 16 may take a variety of forms and may be structured in a variety of ways in addition to the configuration shown in FIG. 1. For example, according to one embodiment of the invention the substrate 16 may have more than two sides on which one or more sensing elements or electronics may be placed. The substrate 16 may be a multi-surface device with sensing elements and electronics on any of multiple surfaces and having multiple vias extending in a variety of geometries to affect electrical contact between surfaces.

In another embodiment of the invention, one or more sensing elements and electronics may be on the same side of the substrate 16. The vias 18 may be arranged accordingly to effect electrical contact between one or more sensing elements and electronics, irrespective of the position of a sensing element and electronics on the substrate 16.

Figure 3:
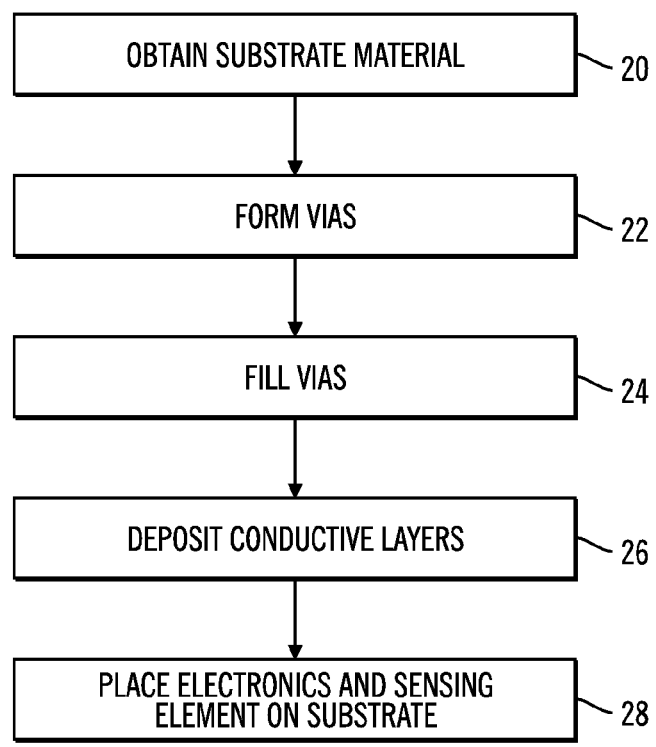
FIG. 3 is a flow diagram of a generalized process for fabricating a sensor substrate according to an embodiment of the present invention.

FIG. 3 shows a generalized process for fabricating a sensor substrate according to an embodiment of the present invention. Although the process detailed in FIG. 3 refers to a substrate, it is to be understood that the process may be applied to a plurality of substrates formed from a single board of substrate material. With reference to FIGS. 1-3, substrate material may be obtained at step 20. At step 22, vias 18 may be formed in the substrate 16 such that a hollow path is created from one side of the substrate 16 to another. The vias may be laser drilled, punched, or formed in other manner common in the industry.

At step 24, the vias 18 may be filled with a material that is electrically conductive such that electrical continuity exists between one side of the substrate 16 and another. In addition, the vias 18 may be filled such that a hermetic seal exists between one side of the substrate 16 and another. At step 26, conductive layers may be deposited onto each side of the substrate 16 that make electrical contact with the vias 18. At step 28, electronics may be placed on one side of the substrate 16 and a sensing element may be placed on another side of the substrate 16, both being placed in such a manner that they make the desired contact with the conductive layers.

Figure 4:
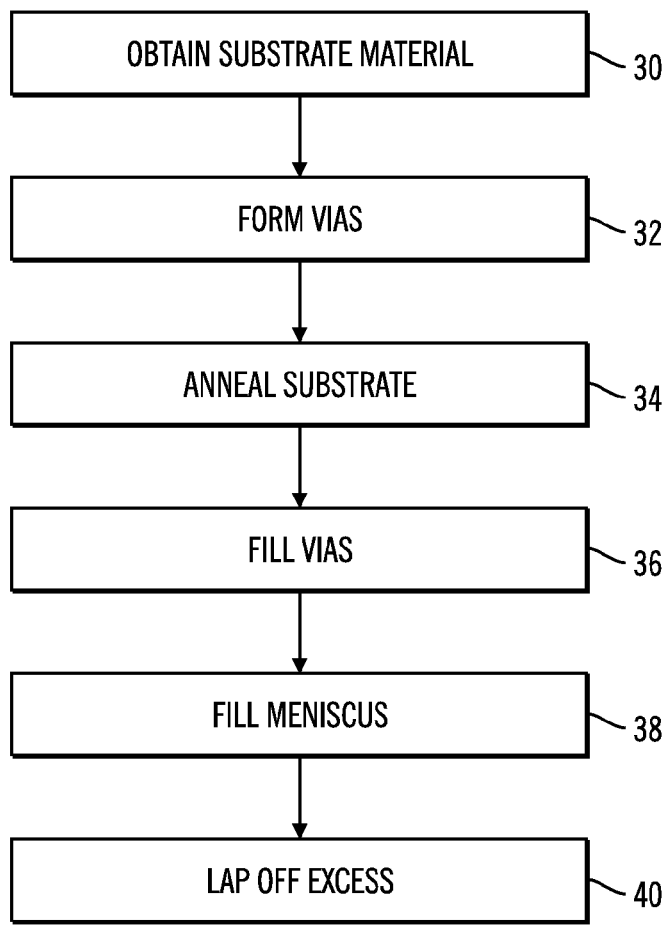
FIG. 4 is a flow diagram of a more detailed process for fabricating a sensor substrate according to an embodiment of the present invention.

FIG. 4 shows a more detailed process for fabricating a sensor substrate according to an embodiment of the present invention. Although the process detailed in FIG. 4 refers to a substrate, it is to be understood that the process may be applied to a plurality of substrates formed from a single board of substrate material.

A variety of fabrication techniques may be used during the fabrication of the sensor substrate. For example, either thin film or thick film fabrication technologies may be used. The generalized process shown in FIG. 4 (or any other process described in the disclosure) is for purposes of illustration only, and should not limit embodiments of the invention in any way.

With reference to FIGS. 1, 2A, 2B, and 4, substrate material may be obtained at step 30. As stated previously, according to a typical embodiment of the present invention, a 92%-96% alumina substrate ($Al_2O_3$) may be used. Alumina is widely used in the microelectronics industry and is available from many resources. For example, a 96% alumina substrate may be purchased from (but is not limited to) COORS, INC.

Although 99.6% alumina is typical in electrode based sensor applications because of its purity, which typically results in enhanced device resistance, 92%-96% alumina may be used in various embodiments for enhanced performance during annealing and testing processes of embodiments of the present invention. On a substrate of greater than 96%, alumina cracks resulting from laser drilling of the vias may not anneal as well as 92%-96% alumina.

A substrate of less than 92% alumina typically has a surface with increased roughness and granularity, which may make it difficult to print on and seal. In addition, testing of a substrate of less than 92% alumina may be difficult because the substrate surface may absorb helium used during leak detection and may be more susceptible to corrosion. Moreover, a substrate of less than 92% alumina is typically darker than 92%-96% alumina and may affect photolithography processes used in embodiments of the present invention.

At step 32, vias 18 may be formed in the substrate 16 such that a hollow path is created from one side of the substrate 16 to another. The vias 18 may be laser drilled, punched, or formed in other manner common in the industry.

At step 34, the substrate 16 may be annealed. If the process used for forming vias 18 results in cracks on the surface of or within the body of the substrate 16, annealing of the substrate 16 may be performed to mend such cracks. According to one embodiment of the present invention, the substrate 16 may be annealed at approximately 1200 C for approximately 16 hours. If the process used for forming vias 18 does not result in cracks on the surface of or within the body of the substrate 16 and hermeticity from one side of the substrate 16 to another is possible without annealing, the annealing step may be avoided.

The vias 18 may be filled at step 36. The vias 18 may be filled with any electrically conductive material that can be packed densely enough to provide hermeticity from one side of the substrate 16 to another. The filler should be electrically conductive so that an electrically conductive path is formed from one side of the substrate 16 to another, allowing electrical contact between components on each side of the substrate 16, such as, for example, sensor electrodes on one side of the substrate 16 and electronic circuitry on another side.

According to one embodiment of the present invention, the vias 18 may be filled with an electrically conductive filler. For example, the vias 18 may be filled with a fritted or fritless ink, such as, but not limited to, a gold or a platinum paste, and/or the like. Fritless ink is generally more desirable than fritted ink in this application because fritted ink typically comprises too many fillers and particulates to facilitate the formation of a densely packed via. In various embodiments, in order to provide hermeticity from one side of the substrate 16 to another, the filling of the via 18 must be such that voids or gaps that would support the development of moisture do not exist within the material used to fill the via 18.

According to one embodiment of the present invention, a 96% alumina substrate, which may be purchased off the shelf from a variety of manufacturers, such as COORS, INC., may be filled with a gold paste. If another type of substrate is used, such as, for example, a 92% alumina substrate, which may be custom made, the substrate may be purchased with the vias already filled with a filler, such as for example, platinum paste.

Figure 5:
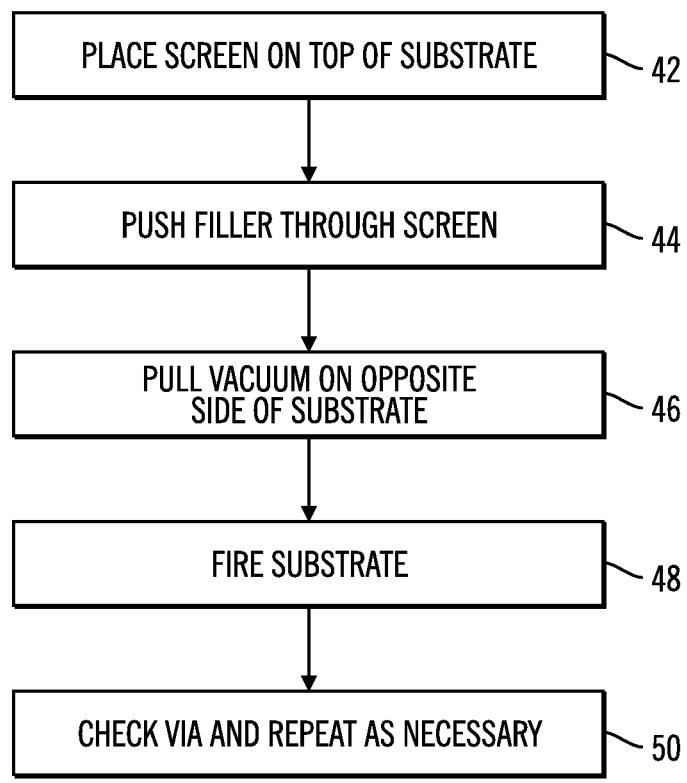
FIG. 5 is a flow diagram of a process for filling vias with a filler according to an embodiment of the present invention.

A process of filling vias with a filler according to an embodiment of the present invention is shown in FIG. 5. With reference to FIGS. 1, 2A, 2B, 4, and 5, at step 42, a screen with a via pattern may be placed on top of the surface of the substrate. A stencil may also be used. At step 44, a filler, such as fritless ink, may be pushed through the screen into the via 18 in a "squeegee" fashion. At step 46, a vacuum may be pulled on a side of the substrate 16 opposite the side on which the filler has been pushed into the via 18 such that the filler coats the walls of the via 18. Filling vias in a vacuum may facilitate intimate contact with surfaces and dense packing.

After the filler has coated the walls of the via 18 in step 46, the substrate 16 may be fired in step 48 so that the filler is hardened, i.e., it becomes solid. At step 50, the via 18 may be checked to determine whether the via 18 is completely plugged. If the via 18 is completely plugged, the process of filling the via 18 according to an embodiment of the present invention is complete. If the via 18 is not completely plugged, steps 42-48 may be repeated as many times as is necessary until the via 18 is completely plugged with the filler.

Figure 6A:
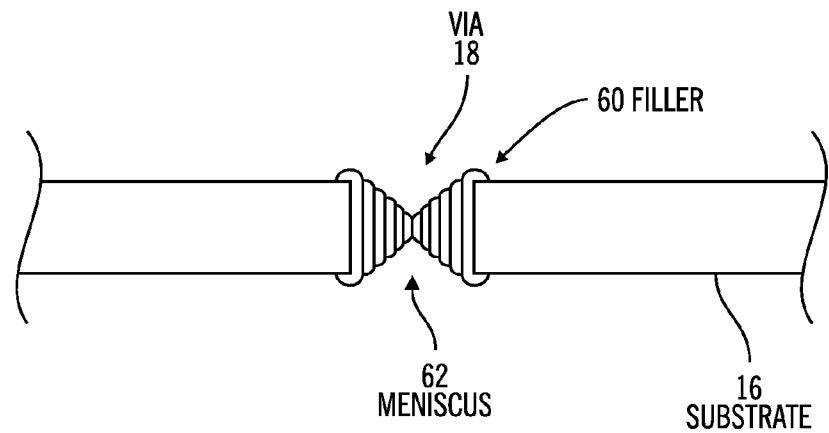
FIG. 6A is a cut-away view of a filled via according to an embodiment of the present invention.

A via 18 filled according to the process of FIG. 5 may be seen in FIG. 6A. A substrate 16 containing a via 18 has been filled with a filler 60. Successive applications of the filler 60 results in layers of the filler 60 extending throughout the hollow area of the via 18 until the filler 60 plugs the via 18 and eliminates any pathway from one side of the substrate 16 to another. A meniscus 62 typically forms on either side of the via 18 after the via 18 has been filled with the filler 60.

With reference to FIGS. 4 and 6A, the meniscus 62 that typically forms during the filling of the vias 18 may be filled at step 38. The meniscus 62 may be filled with the same filler 60 that was used to plug the vias 18.

Figure 7:
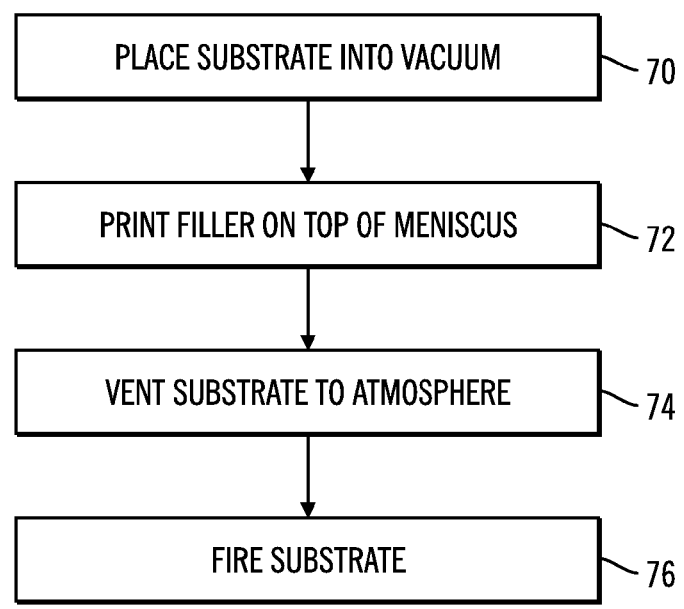
FIG. 7 is a flow diagram for filling a meniscus according to an embodiment of the present invention.

FIG. 7 shows a process for filling the meniscus 62 according to an embodiment of the invention. With reference to FIGS. 4, 6A, and 7, at step 70, the substrate 16 may be put into (or otherwise exposed to) a vacuum. At step 72, a filler 60 may be printed onto the top of the meniscus 62. The printing process used may be the same process detailed earlier (e.g., FIG. 5) for filling the vias 18 or may be another suitable process. At step 74, the substrate 16 may be then vented to atmosphere. Venting the substrate 16 to the atmosphere introduces an atmospheric pressure on the filler 60, which may push down on the filler 60 in the meniscus 62 and displaces any gap that might be in the meniscus 62 or via 18.

At step 76, the substrate 16 may be fired such that the filler 60 in the meniscus 62 is hardened. Firing of the substrate also burns off any organics, solvents, or other impurities. According to one embodiment of the present invention, if the filler 60 used is a fritless ink such as, for example, gold or platinum paste, the substrate 16 may be first fired at 300-400° C. to burn off organics, solvents, or other impurities. The substrate 16 subsequently may be fired at 900-1000° C. At 900-1000° C., the filler 60 may sinter. The firing time may typically be a few hours for every firing cycle. After firing the filler 60 to sinter the filler 60, the substrate 16 may be cooled such that the filler 60 hardens. In some embodiments, cooling must be done at a rate slow enough such that the substrate 16 does not crack, which would compromise the hermeticity of the device. Steps 70-76 may be repeated as often as necessary to fill the meniscus 62 and the layers of filler 60 that extend above the substrate. A substrate 16 with a filled via 18 and a filled meniscus 62 may be seen in FIG. 6B.

Figure 6B:
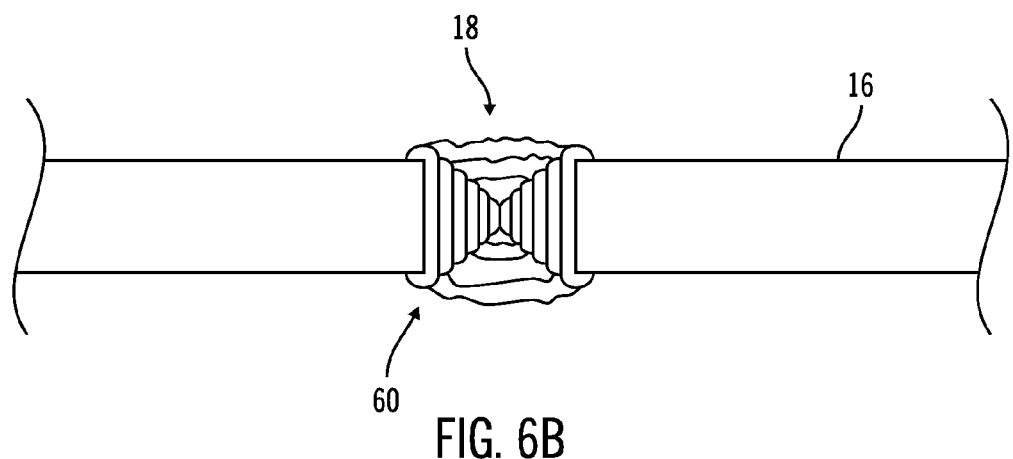
FIG. 6B is a cut-away view of a filled via and a filled meniscus according to an embodiment of the present invention.
Figure 8:
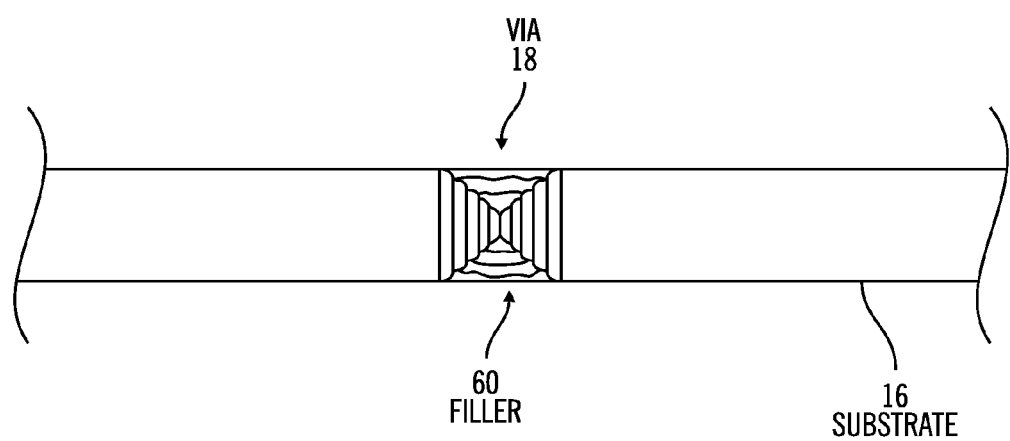
FIG. 8 is a cut-away view of a hermetically filled via with excess filler from a via and a meniscus lapped off according to an embodiment of the present invention.

With reference to FIGS. 4, 6A, and 6B, at step 40 the excess filler 60 that extends above the surface of the substrate 16 resulting from the filling of the vias 18 and the meniscus 62 may be lapped off so that the filler 60 is even with the surface of the substrate 16. The filler 60 may be lapped off using tools and techniques common in the industry so long as the hermetic integrity of the substrate 16 is not compromised. A substrate 16 with excess filler 60 lapped off and hermetically sealed vias 18 may be seen in FIG. 8.

Thus, subsequent to step 40 in FIG. 4, a process according to embodiments of the present invention has generated a substrate 16 that is hermetically sealed from one side to another. With reference to FIGS. 1-8, it should be understood at this point that the fabrication of the substrate 16 for hermeticity is not limited to the process described (e.g., FIG. 4). Other steps or processes may be introduced, or steps may be eliminated, without departing from the spirit and scope of embodiments of the present invention. For example, depending on the type of filler 60 used to fill the vias 18 and the meniscus 62, the annealing steps and the firing steps may be performed at the same time. Other variations in the process are also possible while still maintaining the essence of embodiments of the present invention.

The substrate 16 with hermetically sealed vias 18 may be used for a variety of applications. According to embodiments of the present invention, the substrate 16 may now be prepared to accept a sensing element on one side of the substrate and electronics on another side of the substrate 16. As before, the substrate 16 may be prepared using a variety of techniques, including (but not limited to), for example, thin film or thick film deposition processes. For purposes of illustration, and not by way of limitation, processes according to embodiments of the present invention will be described below using thin film deposition techniques.

Electronics may be affixed to one side of the substrate 16 and may take a variety of forms. For example, the electronics may take the form of an integrated circuit (IC), such as, for example, an ASIC, a microcontroller, or a microprocessor. Alternatively, the electronics may take the form of discrete components.

Figure 9:
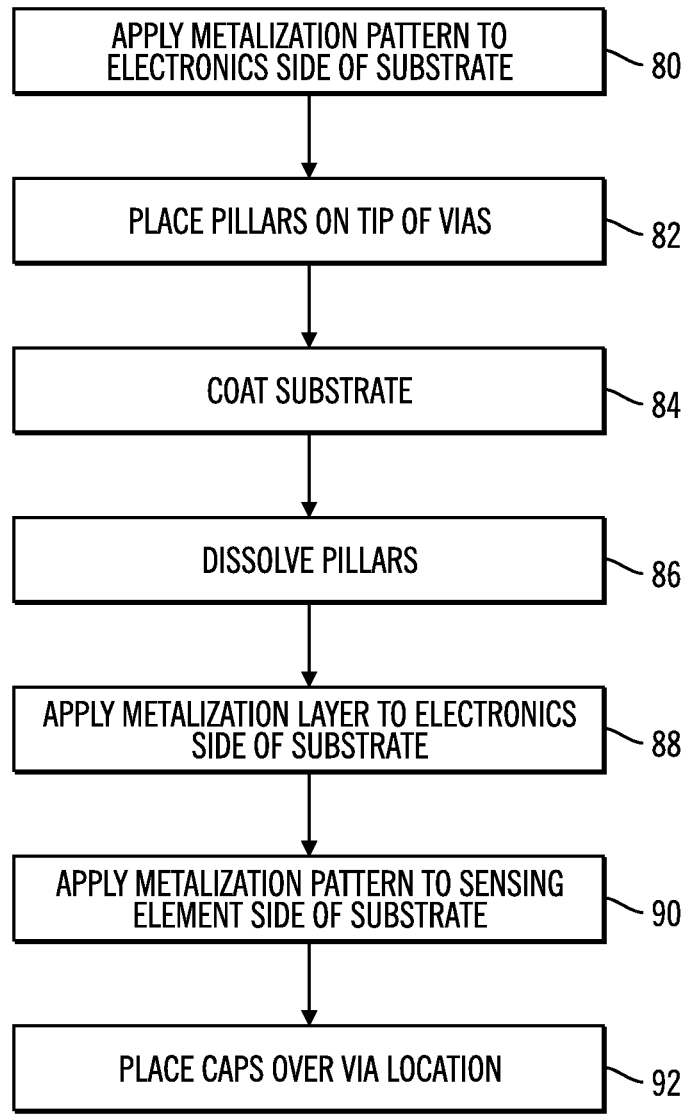
FIG. 9 is a flow diagram of a process for preparing one side of a substrate to accept an IC and another side to accept a sensing element according an embodiment of the present invention.

In addition, a sensing element may be affixed to another side of the substrate 16. FIG. 9 shows a process according to embodiments of the present invention for preparing one side of the substrate 16 (e.g., FIG. 8) to accept an IC and another side to accept a sensing element.

With reference to FIGS. 1-9, at step 80, a side of the substrate 16 being prepared for an IC may have a metallization pattern applied to it using standard resist photolithography or other techniques common in the industry. This layer of metallization is the conductor that provides continuity from the portion of a via 18 on the sensing element side of the substrate 16 to a bonding pad on an IC side of the substrate 16. In practice, this layer may actually be two, three, or more layers. For example, the metallization layer may be a titanium-platinum layer or the like. Alternatively, the metallization layer may be a titanium-platinum-titanium layer or the like. The pattern may correspond to the pins of the IC or may be some other pattern depending on the desired application.

At step 82, aluminum pillars 100 may be placed on top of the vias 18. A ceramic or other material mask (not shown) may be laser drilled, punched or otherwise worked to form openings corresponding to the via pattern on the substrate. According to one embodiment of the present invention, the openings may be 20-25 microns deep. The mask then may be affixed to the substrate 16 on top of the metallization pattern applied during step 80. Then aluminum may be deposited through the openings to form pillars 20-25 microns high. Once the aluminum pillars 100 have been formed, the mask may be removed, leaving the 20-25 micron aluminum pillars 100 on top of the vias 18. A substrate 16 with aluminum pillars 100 formed on top of the vias 18 according to an embodiment of the present invention may be seen in FIG. 10A.

Figure 10A:
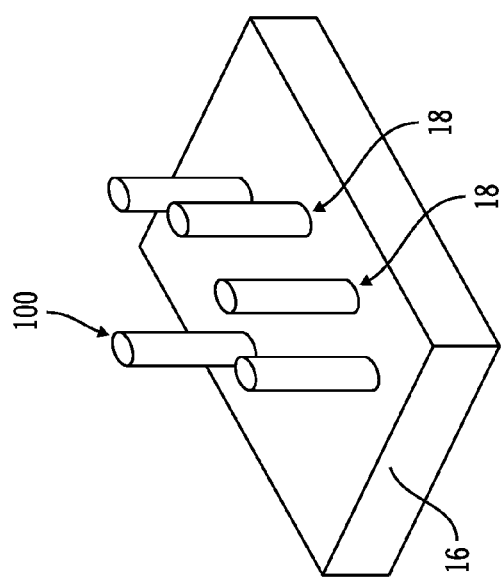
FIG. 10A is a perspective view of a substrate with aluminum pillars formed on top of vias according to an embodiment of the present invention.

With reference to FIGS. 9 and 10A, after step 82, the entire substrate 16 may be coated with an alumina coating at step 84. According to one embodiment of the present invention, the entire substrate 16 may be put into a vacuum chamber and blanket coated with an alumina coating. A variety of processes may be used to blanket coat the substrate 16 with alumina. For example, chemical vapor deposition (CVD), epitaxial deposition, sputtering, or evaporation may be used to blanket coat the substrate 16 with the alumina coating. Alternatively, ion beam assist deposition (IBAD) may be used. IBAD is a combination of two distinct operations: physical vapor deposition combined with bombarding the surface of the substrate 16 with low energy ions. Bombarding the surface of the substrate 16 with low energy ions may allow for better adhesion and higher density of the alumina coating.

Using an IBAD process to coat the substrate 16 with alumina may provide pin-hole free layers of alumina, which enhances the overall hermeticity of the device. In other words, coating the substrate 16 with alumina using the IBAD process may prevent the transmission of vapor, moisture, fluids, or other elements that would compromise the hermetic integrity of the device.

According to one embodiment of the invention, the alumina coating may be 12 microns deep. Consequently, at the end of step 84, the substrate 16 will have aluminum pillars 100 rising 8-13 microns above a 12 micron alumina sheet. A configuration according to this embodiment of the present invention may be seen in FIG. 10B.

Figure 10C:
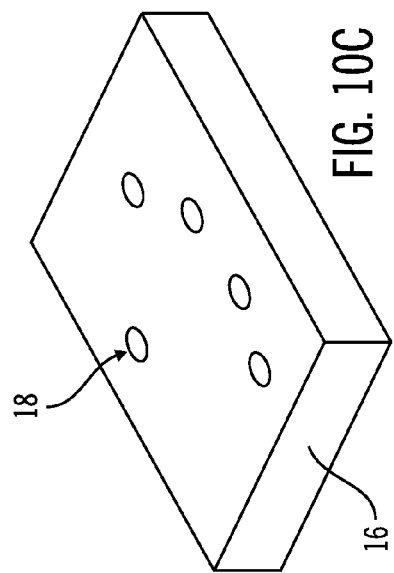
FIG. 10C is a perspective view of a substrate with pillars removed according to an embodiment of the present invention.
Figure 10B:
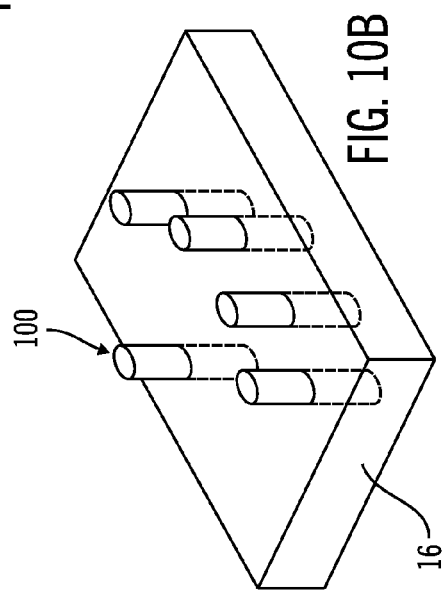
FIG. 10B is a perspective view of a substrate with aluminum pillars formed on top of vias coated with an alumina coating according to an embodiment of the present invention.

With reference to FIGS. 9 and 10B, at step 86, the entire substrate 16, including the alumina coating and the aluminum pillars 100, may be put into a dissolving solution such as, for example, ferric chloride ($FeCl_3$) or other solution strong enough to dissolve the aluminum pillars 100 but mild enough not to attack the alumina coating. Thus, after the aluminum pillars 100 dissolve, the substrate 16 will be covered with an alumina coating 12 microns high with recesses permitting access to the vias. This configuration may be seen in FIG. 10C.

With reference to FIGS. 9 and 10C, at step 88, the metallization layer supporting the IC and any other components being affixed to the electronics side 14 of the substrate 16 may be applied. Any suitable metal may be applied using any suitable process. For example, a metallization using gold (or the like) may be applied with a thin film process. The pattern may take a variety of shapes. For example, according to one embodiment of the invention, the pattern may resemble a "ring" or a "racetrack."

In addition, the gold may fill the recesses created by the aluminum pillars 100 that were previously dissolved. In various embodiments, hermeticity will generally not be required at this layer since the substrate has already been hermetically sealed by this point in the process of such embodiments. Accordingly, the metallization layer may be 6000 to 10000 angstroms. Once this layer of metallization has been applied, the IC, and any other components, such as, for example, capacitors, may be wired bonded or otherwise connected to the pads. Additionally, any other component, such as a lid for the electronics, for example, may be affixed to the electronics side of the substrate subsequent to step 88.

At step 90, a side of the substrate 16 being prepared for a sensing element may be provided with a metallization pattern. A variety of techniques may be used to apply the metallization pattern to the side of the substrate being prepared for a sensing element. For example, a metallization pattern may be applied to the substrate 16 by etching the metallization pattern onto the substrate 16. Alternatively, a metallization pattern may be applied to the substrate 16 using common photoresist techniques.

According to one embodiment of the invention, if common photoresist techniques are used, a photoresist may first be applied to the substrate. The photoresist may be a positive resist, which becomes soluble when interacting with light, or a negative resist, which becomes insoluble when interacting with light. If a positive resist is used, a mask may be put over the photoresist and then the mask and the photoresist may be exposed to light. Thus, light going through openings on the mask solubilizes the unmasked portions of the photoresist. Then, the mask may be washed off, and, consequently, the substrate will have a cured coating of photoresist where the unmasked photoresist was exposed to light. A photoresist corresponding to an electrode pattern according to one embodiment of the invention may be seen in FIG. 11. The electrodes may have tie bars or the like to provide a conductive path for electroplating. The working and counter electrodes may be metallized.

Next, the cured photoresist may be metallized using a variety of techniques. Any thin film deposition technique may be used, such as, for example, sputtering. Thus, according to one embodiment of the invention, the substrate may be put into a vacuum, then, sputtered with a first metal, such as, for example, titanium, and then sputtered with a second metal, such as, for example, platinum. Accordingly, a conductive layer may be placed between the vias and alumina caps in order to maintain electrical conductivity.

Next, the photoresist may be washed away. For example, the photoresist may be put into an acetone ultrasonic bath or the like. Thus, a photoresist not cured during exposure to light by the mask will dissolve and metal deposited on the uncured photoresist will be washed away.

Figure 11:
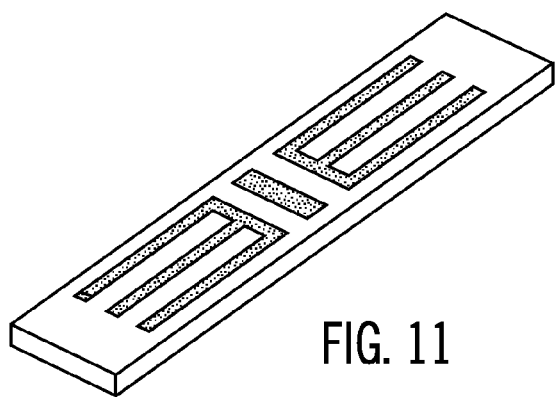
FIG. 11 is a perspective view of a photoresist corresponding to an electrode pattern according to an embodiment of the invention.

With reference to FIGS. 9-11, at step 92, caps may be placed over the via locations. Oxygen reduction may occur at the working electrodes and create hydroxyl ions, thus creating an alkaline local environment. As the device operates, the hydroxyl ions may attack the electrode/via interface. The electrode/via interface initially may be hermetic, but can be broken down if the hydroxyl ions interact with the via 18 for an extended period. Thus, to extend life of the via 18 a cap (not shown) may be placed over the via 18 to keep current from the electrochemical process of the hydroxyl ions from entering the via 18, thus extending life of the via 18 and improving reliability of the via 18. In other words, caps may be used to prevent byproducts of detection electrochemistry from compromising via hermeticity by preventing corrosive attack of both the via 18 and the annealed surfaces of a laser drilled opening.

A variety of techniques may be used to place a cap over the vias 18. For example, alumina caps may be deposited over the via 18 using an IBAD process. A shadow mask may be used during the process similar to the technique used to apply the aluminum pillars 100. Caps may be formed with a positive shadow mask, which may be used where alumina deposited through an aperture remains in place on a finished substrate. The cap position may be adjusted (e.g., a length of the cap may be adjusted along the electrode) changing the configuration of the active electrodes to the windows. The sensitivity of the sensor can depend on the cap position, or the resulting position of the active electrode to the window.

As an alternative to placing caps over vias 18, caps may be placed over electrodes to inhibit oxygen reduction at the electrodes. According to embodiments of the invention, caps placed over the vias 18 or the electrodes may be about 18 microns in thickness.

Once an electronics side 14 (FIG. 1) of the substrate 16 and a sensing element side 12 (FIG. 1) of the substrate 16 has been prepared to accept electronics and a sensing element, respectively, electronics and a sensing element may be affixed to the substrate. A process for affixing an IC to the electronics side of the substrate 16 may be shown in FIG. 12.

Figure 12:
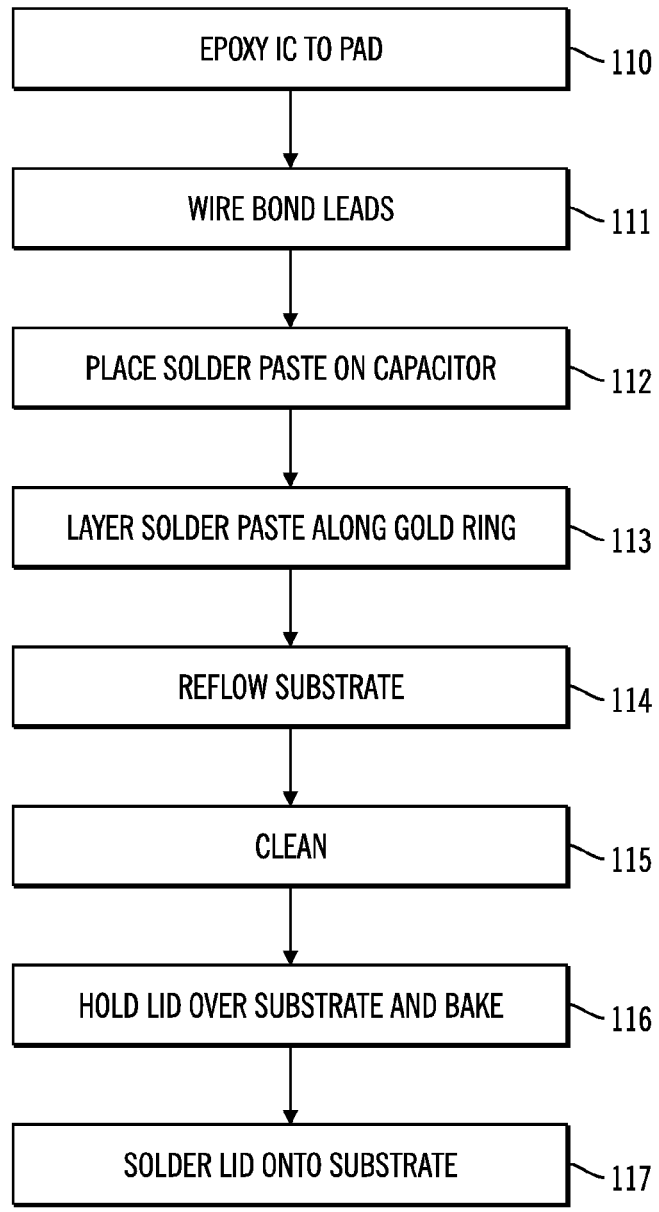
FIG. 12 is a flow diagram of a process for affixing an IC to an electronics side of a substrate according to an embodiment of the present invention.

With reference to FIGS. 1 and 12, at step 110, an IC may be epoxied or otherwise adhered to a rectangular pad in the center of the substrate 16. At step 111, leads of the IC may be wired bonded to the gold pads earlier formed on the electronics side 14 of the substrate 16.

According to some embodiments of the invention, a capacitor may be used in connection with the IC. The capacitor may serve as a power supply instead of a battery and may be large enough to maintain a DC voltage in between pulses. If a capacitor is used, at step 112 a solder paste may be placed on the capacitor and the capacitor may be put into position on the substrate 16.

At step 113, a layer of solder paste may be placed along the entire gold ring previously deposited on the electronics side 14 of the substrate 16. At step 114, the entire substrate 16 may be reflowed at temperature, including the solder paste deposited on the gold ring. The entire substrate 16 may then be put through cleaning cycles at step 115 to remove residual material, such as flux residue from solder paste.

According to one embodiment of the invention, a lid may be placed over the electronics. At step 116, the lid may be held by a fixture over the substrate 16 and the substrate 16 may be baked to remove moisture. For example, the substrate 16 may be baked at 150° C. for 12 hours at less than 1 torr to reduce moisture to 5000 ppm or less.

At step 117, the lid may be soldered onto the substrate 16. The lid may be formed from a solid gold sheet, typically (but not limited to) about 3 mils thick. In some embodiments, the lid may include a lip, such as (but not limited to) a bathtub shaped lip or the like. After the baking process of step 116, the lid and substrate 16 may be put into a helium atmosphere (some helium, such as, for example, 1 atmosphere, may be left in the lid for reasons to be discussed below in connection with leak testing) with very low oxygen and very low moisture. Thus, because of the solderability of gold and the absence of any oxidation due to the low oxygen atmosphere, the lid may be soldered onto the electronics side 14 of the substrate 16 without using solder without flux. Consequently, no flux residue will exist on the substrate 16 subsequent to soldering the lid to the substrate 16. The absence of any residue on the substrate 16 may be desirable because any residue may promote condensation or water vapor between IC pads, thus providing a leakage path. On an IC, there is typically only a 0.002-0.003 space between IC pads. In various embodiments, leakage currents should be kept less than 50 pico amps in order to be distinguishable from, for example, the currents generated by an electrochemical cell used as a sensing element.

Figure 13:
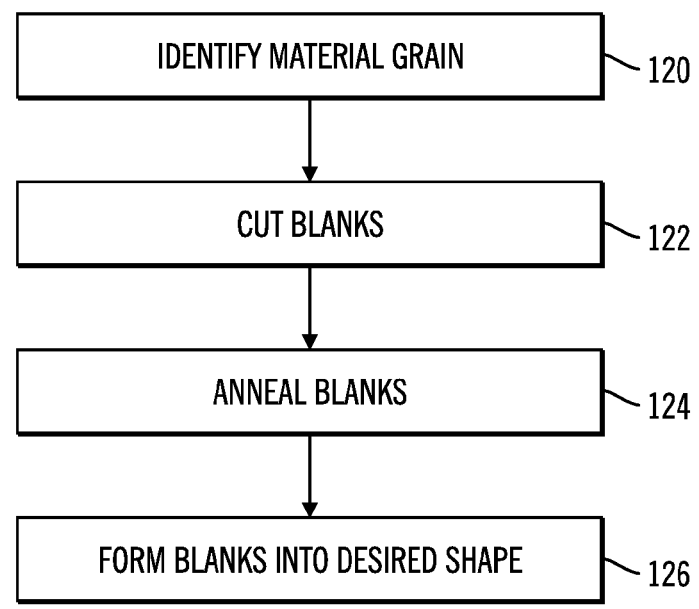
FIG. 13 is a flow diagram of a process for forming a lid according to an embodiment of the present invention.

A process for forming a lid is shown in FIG. 13. With reference to FIGS. 1 and 13, in order to prevent the lid from tearing and developing holes, the grain of the material may be identified such that a blank may be properly cut and annealed. Thus, the proper malleability of the material may be achieved. The grain may be due to mechanical stress from a rolling process. Accordingly, at step 120, a grain of a material is identified. According to one embodiment of the invention, the longer dimension of the material is identified. At step 122, blanks squares or rectangles are cut from the material. The blanks may be annealed at step 124. At step 126, the blanks may be formed into the desired shape. In a case where gold (or the like) is the material used, step 126 may be speed controlled because gold hardens very quickly.

In addition, if the form of the lid is to be a bathtub shape as described above, the lid may have a small flange to provide a good seal. The flange may be 4-5 mils thick, or a wider dimension than the thickness of the area of the electronics on the electronics side 14 of the substrate 16. For example, in some embodiments, the gold track on the substrate 16 may be 4 mm wide. In other embodiments, thick, wide lid walls may be used as an alternative to the flange. In some embodiments, the lid may have a small draft to allow a capacitor to be near its end.

Figure 14:
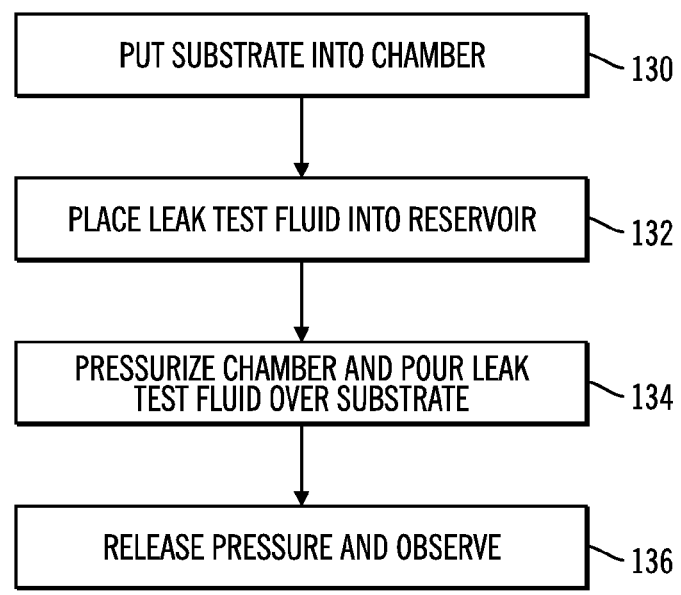
FIG. 14 is a flow diagram of a process for performing a gross leak test according to an embodiment of the present invention.

In some embodiments, the substrate 16 may be subjected to leak testing. Gross leak testing and/or fine leak testing may be performed. Leak testing may be performed in a variety of ways. For example, a process for performing a gross leak test according to an embodiment of the present invention is shown in FIG. 14. With reference to FIGS. 1 and 14, at step 130, the substrate 16 may be put into a chamber. According to one embodiment of the invention, the chamber may have a recess for the substrate 166 and a reservoir for a leak test fluid, such as, for example, Freon. At step 132, the leak test fluid is placed in the reservoir. At step 134, the chamber may be pressurized with helium and the leak test fluid is poured into the recess. For example, the chamber may be pressurized at 150 psi (10 atmospheres) and kept at this level for 12 hours. At step 136, the pressure may be released and the fluid may be observed for bubbles. An absence of bubbles may indicate that there are no gross leaks in the substrate.

In some embodiments, a fine leak test may be performed. For example, a process for performing a fine leak test according to an embodiment of the present invention may include putting the substrate 16 into a vacuum chamber and observing helium leaks with a mass spectrometer. Helium exists in the lid previously attached to the electronics side 14 of the substrate 16. Thus, any helium observed may indicate a fine leak in the substrate 16.

Figure 15:
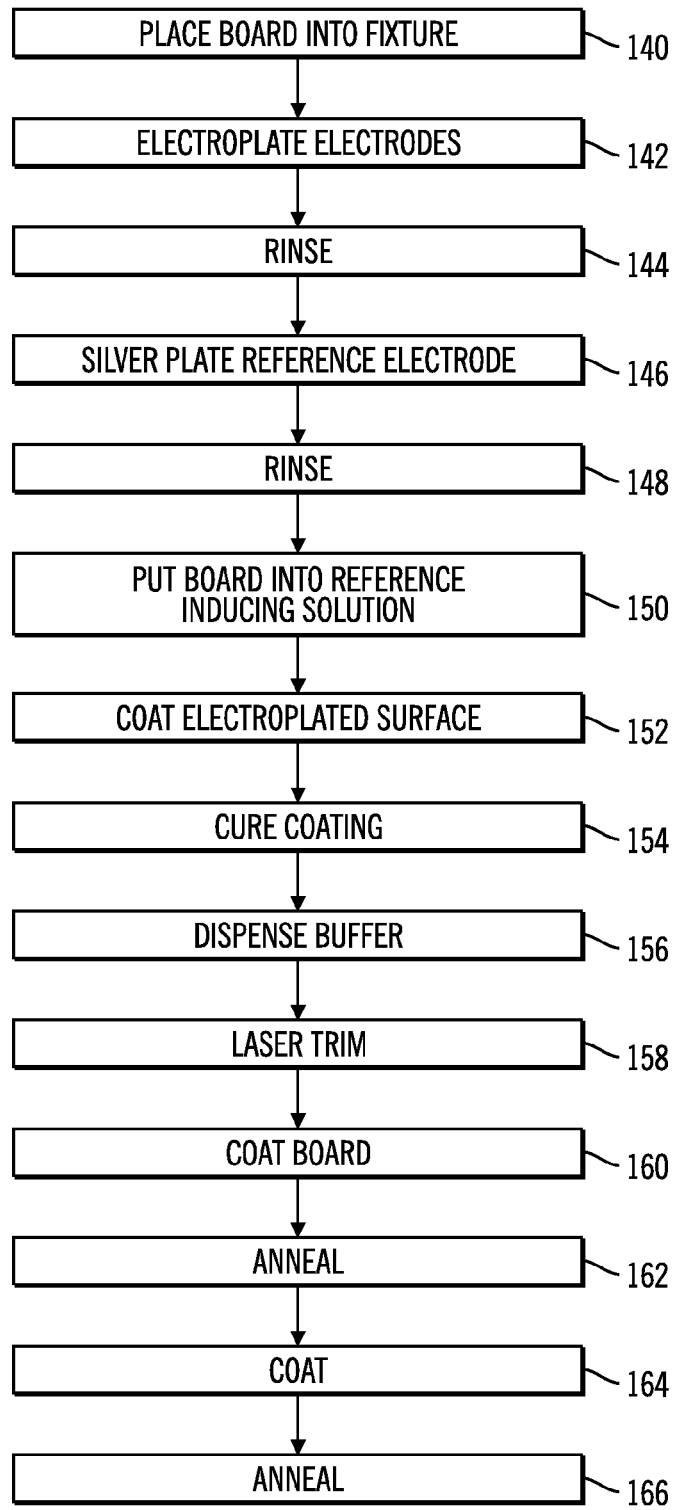
FIG. 15 is a flow diagram of a process for electroplating and coating the substrate according to an embodiment of the present invention.

Once a substrate 16 has passed a gross leak test and a fine leak test, the substrate 16 may be put through a final electroplating and coating process. A process for electroplating and coating the substrate according to an embodiment of the present invention is shown in FIG. 15. To describe the process according to the embodiment of the present invention shown in FIG. 15, the description will refer to a board of substrate material from which a plurality of substrates may be formed.

At step 140, the board may be placed into a fixture for electroplating. At step 142, the electrodes may be electroplated with a metal. For example, a noble metal probe may be used to deposit a first solution of chloroplatinic acid onto the electrodes, i.e., platinum may be deposited onto the electrodes. This is typically called platinum blackening. According to one embodiment of the invention, four out of the five electrodes, i.e., the first and second working electrodes and the first and second counter electrodes may be blackened with platinum. After the electrodes have been blackened with platinum, the board may be rinsed at step 144. A variety of fluids may be used to rinse the board.

At step 146, according to an embodiment of the present invention, the reference electrode may be silver plated using a silver-plating solution. At step 148, the board may be rinsed again.

At step 150, the board may be put into a solution, such as, for example, a dilute hydrochloric acid solution, to make an electrochemical reference. According to one embodiment of the present invention, the hydrochloric acid will react with the reference electrode and the counter electrodes, generating a potential difference between the reference electrode and the counter electrodes that may be used as a reference voltage.

At step 152, the surface of the board that has been electroplated may be coated. A variety of techniques may be used to coat the surface of the board. For example, the surface of the board may be spin coated using a polymer such as hydroxyethel methacholate (HEMA) or polyhydroxyethel methacholate (PHEMA). This coating may form the basis of an electrolyte layer that defines how much oxygen may flow to an electrode. It may act like a valve and may be flow insensitive such that the amount of oxygen flowing to the electrode remains substantially constant.

At step 154, the coating may be cured using a photomask, such as a negative photoresist, and exposure to ultraviolet light. At step 156, a sterile bicarbonate buffer may be dispensed onto the polymer. The buffer may be isotonic such that it inhibits communication with water and provides for an osmotic exchange. The buffer may also have sodium chloride in it such that it provides electrolytic properties to the polymer. According to an embodiment of the present invention, small drops may be placed onto the polymer such that the drops do not flow over the side of the board. The spaces between the drops may be filled in with more drops and the drops may soak into the polymer.

At step 158, the board may be laser trimmed to remove all traces connecting the electrodes. Thus, subsequent to step 158, the electrodes will be separated. At step 160, the board may be coated again using any of a variety of techniques, such as spin coating, with an adhesion promoter, such as silane.

At step 162, the coating applied at step 160 may be annealed so that the coating cures. At step 164, the board may be yet again coated using any of a variety of techniques, such as spin coating, with an insulating material, such as silicon rubber, and annealed again at step 166. Steps 164 and 166 prevent fluid components, such as those that may be found in blood, from penetrating any circuitry on the substrate. In addition, using steps 164 and 166, electric currents remain within the boundaries of the substrate.

Figure 16:
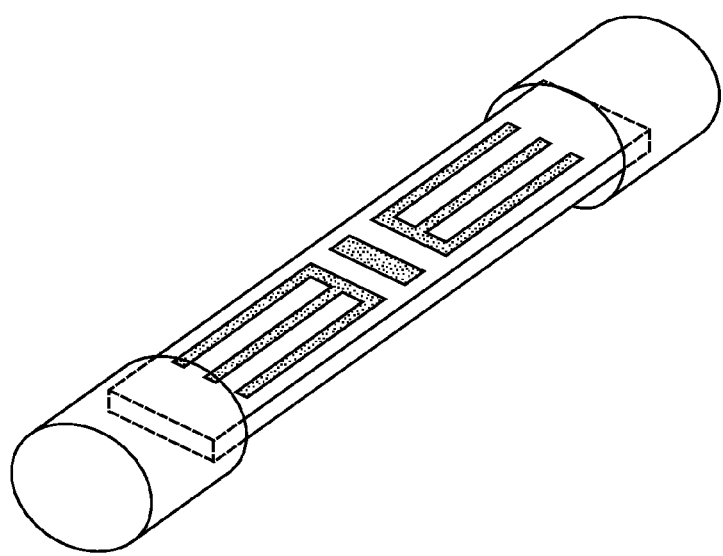
FIG. 16 is a perspective view of a finally assembled sensor substrate according to an embodiment of the invention.

Subsequent to step 166, the board is complete. The completed board may be separated into individual modules. For example, the completed board may be put onto a waxed glass plate and diced with a dicing saw to cut the individual modules. At step 166, leads that may extend to another device such as a pump or other electronics may be welded onto each module. Additionally, end caps or beads, which may be formed from molded silicon, may be placed at the end of each module. A finally assembled sensor substrate may be seen in FIG. 16. According to one embodiment of the invention, ninety-four modules may be made from a board with dimensions two inches by two inches.

Figure 17:
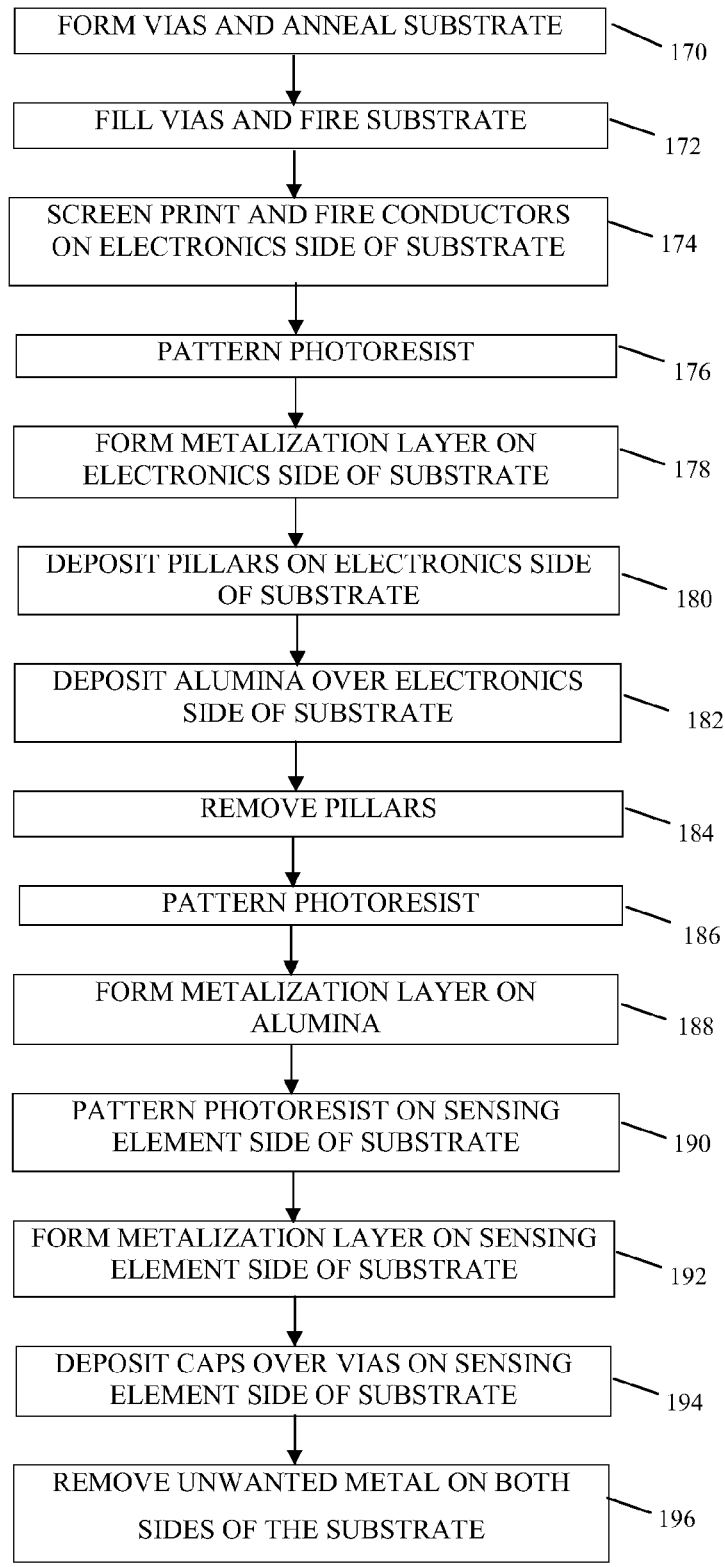
FIG. 17 is a flow diagram of a generalized process for fabricating a sensor substrate according to an embodiment of the present invention.

A generalized process for fabricating a substrate according to another embodiment of the invention may be seen in FIG. 17. With reference to FIGS. 1-17, at step 170, vias 18 may be formed on a substrate 16 and the substrate 16 may be annealed. The vias 18 may be formed using laser drilling. The substrate 16 may be a 92%-96% alumina substrate.

At step 172 the vias 18 may be filled and the substrate 16 fired. The vias 18 may be filled with a variety of conductive materials such as, for example, gold or platinum. In addition, the vias 18 may be filled using a vacuum screen printing process. Step 172 may be repeated until the vias 18 are filled. Once the vias 18 are filled, the vias 18 may be checked for hermeticity.

At step 174, an electronics side 14 of the substrate 16 may be screen printed and conductors may be fired upon it. According to one embodiment of the invention, the conductors may be fired using platinum and a thick film process.

At step 176, a photoresist may be patterned on the electronics side 14 of the substrate 16. Next, at step 178, a metallization layer may be formed on the electronics side 14 of the substrate 16. For example, titanium and platinum may be deposited on the electronics side 14 of the substrate 16 using a DC sputtering process. The photoresist may then be lifted from the substrate 16.

At step 180, aluminum pillars 100 may be deposited on the electronics side 14 of the substrate 16. According to an embodiment of the invention, the aluminum pillars 100 may be 30-micron pillars and may be deposited using a shadow mask and a vacuum evaporation technique.

At step 182, alumina may be deposited over the electronics side 14 of the substrate 16. The alumina deposited may be an 18-micron layer over the entire side of the substrate 16 and may be deposited using an ion beam assisted vacuum evaporation process. At step 184, the aluminum pillars 100 deposited at step 180 may be removed using ferric chloride. At step 186, a photoresist may be patterned on top of the 18-micron layer of alumina.

At step 188, another metallization layer may be placed on top of the alumina surface. According to an embodiment of the invention, titanium, platinum, and gold may be deposited on top of the alumina surface using a DC sputtering process. The photoresist may then be lifted from the substrate 16.

At step 190, a photoresist may be patterned on a sensing element side 12 of the substrate 16. The sensing element side 12 of the substrate 16 may or may not be the same side as the electronics side 14 of the substrate 16. At step 192, a metallization layer may be formed on the sensing element side 12 of the substrate 16. According to one embodiment of the invention, titanium and platinum may be deposited on the sensing element side 12 of the substrate 16 using a DC sputtering process. The photoresist may then be lifted from the substrate 16.

At step 194, caps may be deposited over the vias 18. According to one embodiment of the invention, a shadow mask may be used to deposit 18-micron alumina caps over vias 18 projected on the sensing element side 12 of the substrate 16 using an ion beam assisted vacuum evaporation technique.

At step 196, unwanted metal existing on either the electronics side 14 of the substrate 16 and/or the sensing element side 12 of the substrate 16 may be removed. According to one embodiment of the invention, unwanted metal may be removed using a shadow mask and an ion mill etching process.

As stated previously, according to an embodiment of the present invention, forming IBAD caps on an electrode side of the substrate 16 may be done with a positive shadow mask. A positive shadow mask may be used where alumna deposited through an aperture remains in place on a finished substrate. A negative shadow mask may be used for applications where apertures or openings define regions that remain free of IBAD aluminum coatings. According to various embodiments, the use of positive and negative imaging of IBAD alumina along with screen-printing via filling and conductor application, and photoresist based thin film metallization may create a substrate possessing conductor and insulator geometries along with materials properties which support chronic, continuous sensing applications and microelectronics packaging in harsh environments such as, for example, the blood stream.

Figure 18:
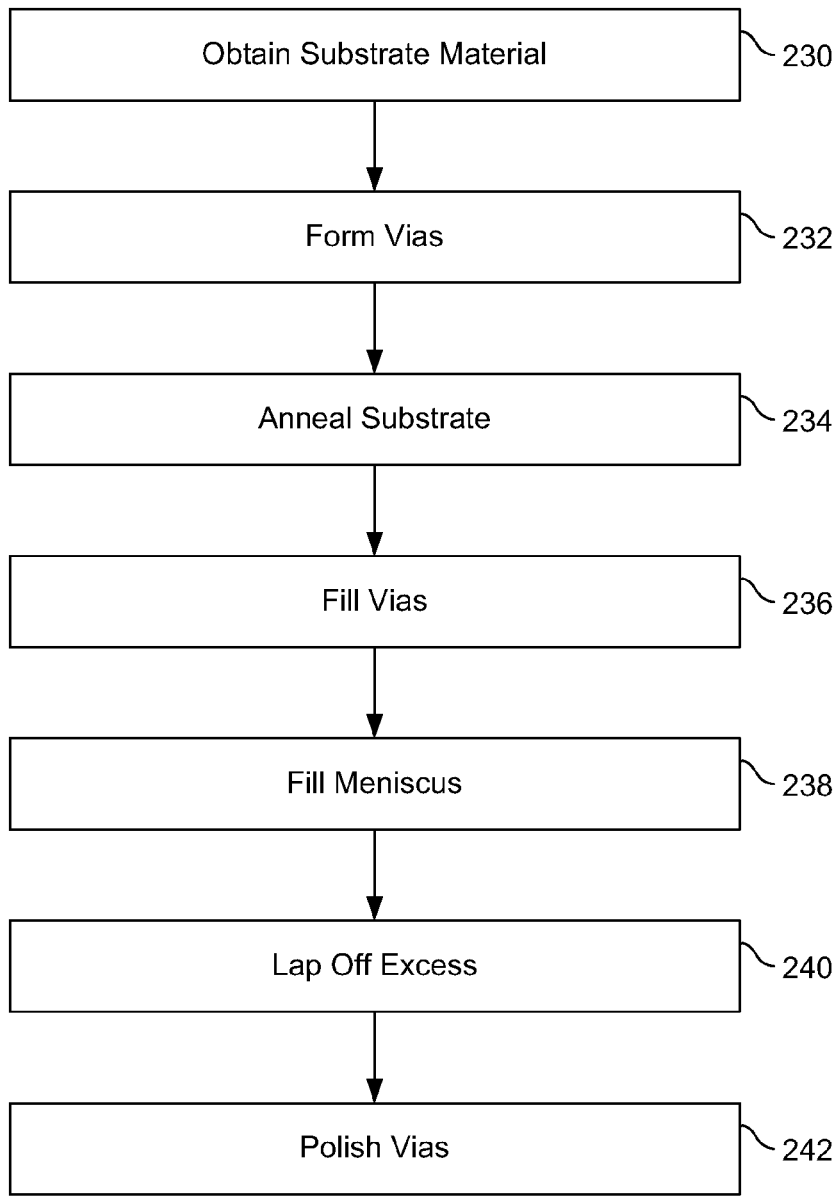
FIG. 18 is a flow diagram of a generalized process for fabricating a sensor substrate according to an embodiment of the present invention.

FIG. 18 shows a process for fabricating a sensor substrate according to an embodiment of the present invention. Although the process detailed in FIG. 18 refers to a substrate, it is to be understood that the process may be applied to a plurality of substrates formed from a single board of substrate material. The process of FIG. 18 and/or the sensor (or other device) produced by such a process may be similar to or employed as an embodiment of any of the processes and/or sensors (or other device) previously discussed (e.g., FIGS. 1-17). Likewise, it should be understood that any of the features of the embodiments of FIGS. 18-21 may be combined or otherwise incorporated into any of the other embodiments of FIGS. 18-21 as well as any other embodiment herein discussed.

With reference to FIGS. 1, 2A, 2B, and 18, substrate material may be obtained at step 230. In some embodiments, a ceramic substrate may be used. In other embodiments, as stated previously, a 92%-96% alumina substrate ($Al_2O_3$) may be used. In other embodiments, other suitable substrate materials may be used including, but not limited to, silicon, glass, composite material, metal, plastic, and/or the like.

At step 232, vias 18 may be formed in the substrate 16 such that a hollow path is created from one side of the substrate 16 to another. The vias 18 may be laser drilled, punched, or formed in other manner common in the industry.

At step 234, the substrate 16 may be annealed. If the process used for forming vias 18 results in cracks on the surface of or within the body of the substrate 16, annealing of the substrate 16 may be performed to mend such cracks. According to one embodiment of the present invention, the substrate 16 may be annealed, for example, as previously described. In further embodiments, the substrate 16 may be annealed at one or more temperatures within the range of approximately 400 degrees Centigrade to approximately 1200 degrees Centigrade for a suitable time period. Furthermore, an annealing procedure may include multiple annealing temperatures in multiple time periods, such as, but not limited to, an initial annealing temperature of approximately 400 degrees Centigrade for approximately 5 minutes, followed by raising the annealing temperature to 500 degrees Centigrade and holding that temperature for approximately 5 minutes, followed by raising the annealing temperature again to approximately 1000 degrees Centigrade and holding that temperature for approximately 20 minutes. In other embodiments, other suitable annealing temperatures and time periods may be used in other suitable single step (single temperature) or multi-step (multiple temperature and time period) procedure. If the process used for forming vias 18 does not result in cracks on the surface of or within the body of the substrate 16 and hermeticity from one side of the substrate 16 to another is possible without annealing, the annealing step may be avoided.

The vias 18 may be filled at step 236. In some embodiments, the vias 18 may filled with an optically transmissive material. In particular embodiments the optically transmissive material must be packed densely enough to provide hermeticity from one side of the substrate 16 to another. The filler should be optically transmissive so that an optical path may be formed from one side of the substrate 16 to another, allowing optical communication between components on each side of the substrate 16, such as, for example, between the illumination device on the electronics side 14 of the substrate 16 and the sensing element on the sensing element side 12 of the substrate 16.

In particular embodiments, the vias 18 may be filled with an optically transmissive filler. For example, the vias 18 may be filled with a fritted material (e.g., fritted glass), quartz, silica, and/or the like. In various embodiments, in order to provide hermeticity from one side of the substrate 16 to another, the filling of the via 18 must be such that voids or gaps that would support the development of moisture do not exist within the material used to fill the via 18.

Various examples of processes for filling the via 18 are discussed in the disclosure, for example (but not limited to) in the description relating to FIG. 5. A via 18 filled according to the process of FIG. 5 may be seen in FIG. 6A in which a substrate 16 containing a via 18 has been filled with a filler 60. Successive applications of the filler 60 results in layers of the filler 60 extending throughout the hollow area of the via 18 until the filler 60 plugs the via 18 and eliminates any pathway from one side of the substrate 16 to another. A meniscus 62 typically forms on either side of the via 18 after the via 18 has been filled with the filler 60.

With reference to FIGS. 18 and 6A, the meniscus 62 that typically forms during the filling of the vias 18 may be filled at step 238. The meniscus 62 may be filled with the same filler 60 that was used to plug the vias 18. Various examples of processes for filling the meniscus 62 are discussed in the disclosure, for example (but not limited to) the description relating to FIG. 7. A substrate 16 with a filled via 18 and a filled meniscus 62 may be seen in FIG. 6B.

With reference to FIGS. 18, 6A, and 6B, at step 240 the excess filler 60 that extends above the surface of the substrate 16 resulting from the filling of the vias 18 and the meniscus 62 may be lapped off so that the filler 60 is even with the surface of the substrate 16. The filler 60 may be lapped off using tools and techniques common in the industry so long as the hermetic integrity of the substrate 16 is not compromised. A substrate 16 with excess filler 60 lapped off and hermetically sealed vias 18 may be seen in FIG. 8. Next in step 242, the vias 18 may be polished to promote optical conductivity of the filler material.

Thus, subsequent to step 242 in FIG. 18, a process according to embodiments of the present invention has generated a substrate 16 that is hermetically sealed from one side to another. With reference to FIGS. 1-18, it should be understood at this point that the fabrication of the substrate 16 for hermeticity is not limited to the process described (e.g., FIG. 18). In other embodiments, other steps or processes may be introduced, or steps may be eliminated. For example, depending on the type of filler 60 used to fill the vias 18 and the meniscus 62, the annealing steps and the firing steps may be performed at the same time.

Electronics may be affixed to one side of the substrate 16, as discussed, for example in (but not limited to) the description relating to FIG. 9, which shows a process according to embodiments of the present invention for preparing one side of the substrate 16 to accept electronics. In some embodiments, the electronics on the electronics side 14 of the substrate 16 may comprise an illumination device, emitter, or the like. Examples of such illumination devices and associated electronics are described in, but are not limited to, U.S. Pat. No. 6,671,527, entitled "Optical Sensor for In Situ Measurement of Analytes"; U.S. Pat. No. 6,994,691, entitled "Injection Apparatus"; U.S. Pat. No. 7,228,159, entitled Optical Sensor Containing Particles for In Situ Measurement of Analytes"; U.S. Pat. No. 7,541,598, entitled "Method and Apparatus for Measuring the Phase Shift Induced in a Light Signal by a Sample"; and U.S. Patent. Pub. No US 2009/0131173, entitled "Sensor for Detection of Carbohydrate," all of which are herein incorporated by reference in their entirety.

In various embodiments, the illumination device may be a light emitting device (LED), Vertical Cavity Surface Emitting Laser (VCSEL), an edge emitting laser (EEL), or the like. In particular embodiments, the illumination device may be an LED, a VCSEL, an EEL, or the like manufactured by Vixar, Inc. In other embodiments, other suitable manufacturers and/or other suitable illumination devices or the like may be employed.

A sensing element may be affixed to another side of the substrate 16, as discussed, for example in (but not limited to) the description relating to FIG. 9, which shows a process according to embodiments of the present invention for preparing one side of the substrate 16 to accept a sensing element. In some embodiments, the sensing element on the sensing element side 12 of the substrate 16 may be one of the sensing elements described in, but not limited to, U.S. Pat. No. 6,671,527, entitled "Optical Sensor for In Situ Measurement of Analytes"; U.S. Pat. No. 6,994,691, entitled "Injection Apparatus"; U.S. Pat. No. 7,228,159, entitled Optical Sensor Containing Particles for In Situ Measurement of Analytes"; U.S. Pat. No. 7,541,598, entitled "Method and Apparatus for Measuring the Phase Shift Induced in a Light Signal by a Sample"; and U.S. Patent. Pub. No US 2009/0131173, entitled "Sensor for Detection of Carbohydrate," all of which are herein incorporated by reference in their entirety.

Figure 21:
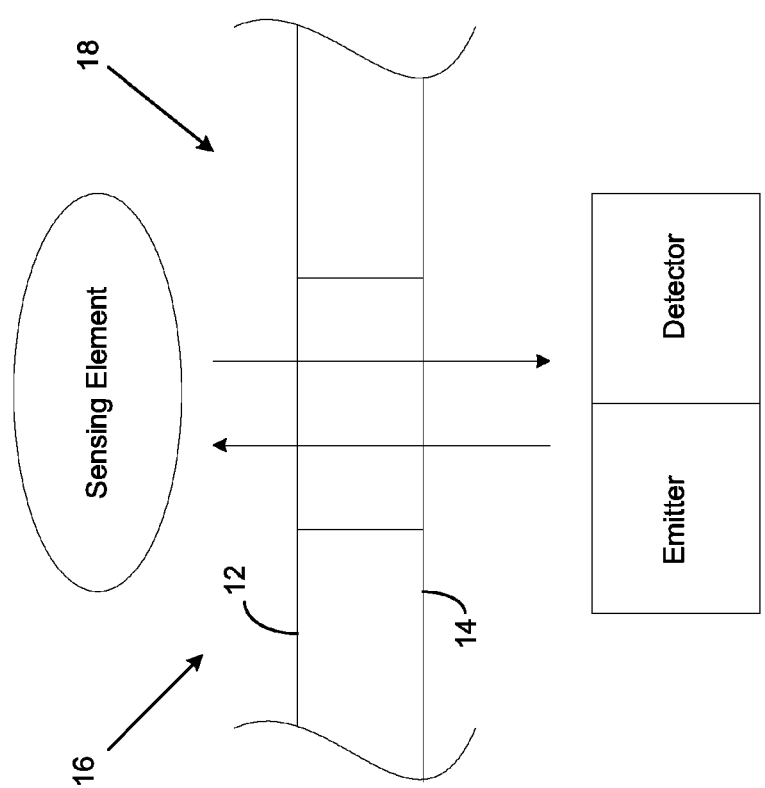
FIG. 21 is a cut-away view of a substrate with a filled via and associated electronics according to an embodiment of the present invention.

In particular embodiments, such as the embodiment shown in FIG. 21, the sensing element may be configured to allow a fluorescence resonance energy transfer (FRET) or the like to sensed, measured, or otherwise detected. In such embodiments, the electronics may include an illumination device (or other emitter) and a sensor, detector, or the like for capturing, measuring, or otherwise detecting a returned fluorescence. Thus in various embodiments, for example, a light emitting device on one side of the substrate 16 may illuminate a sensing element on another side of the substrate 16 through the optically transmissive material in the via 18. A sensor, detector, or the like may detect a returned fluorescence from the sensing element through the via 18.

According to one exemplary method that monitors or otherwise senses a glucose binding event (or similar event) using through FRET, an assay may be based on competitive binding of glucose and a glucose analogue (ligand) to a naturally occurring glucose receptor. These macromolecules may be contained within the sensing element. The sensing element may be configured such that glucose may be allowed to diffuse in and out as function of the changes in glucose. By placing a specially selected pair of a fluorescent molecule on the receptor and a dye on the ligand, a distance between the receptor and the ligand can be determined, for example, through advanced lifetime spectroscopy. The distance will change in a reproducible and known manner with changes in glucose concentration.

Figure 19A:
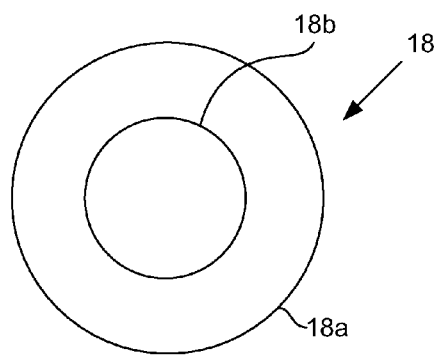
FIGS. 19A-19D show filled vias according to various embodiments of the present invention.
Figure 19B:
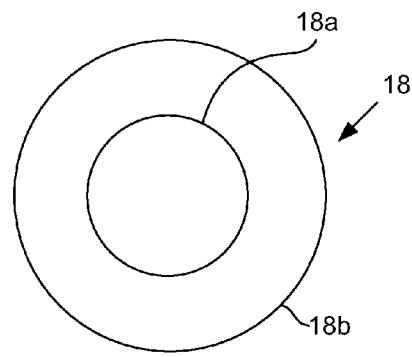
Figure 19C:
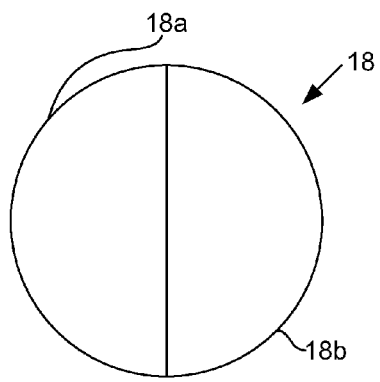
Figure 19D:
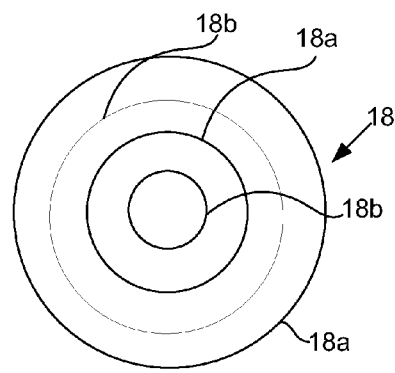

In various embodiments, the vias 18 may be filled with an optically transmissive material (e.g., fritted glass, quartz, silica, and/or the like) and an electrically conductive material (e.g., gold, platinum, indium tin oxide, and/or the like). For example, as shown in FIG. 19A, a first region 18a of the filler material in the via 18 may be an optically transmissive material, and the second region 18b of the filler material in the via 18 may be an electrically conductive material. The second region 18b may be concentrically arranged in the first region 18a. In other embodiments, for example, as shown in FIG. 19B, the first region 18a containing optically transmissive material may be concentrically arranged in the second region 18b containing electrically conductive material. In further embodiments, the via 18 may include one or more concentric first regions 18a interposed between second regions 18b, as exemplified in FIG. 19D.

It should be noted, that the arrangements of FIGS. 19A and 19B are exemplary and are not limited to two regions, but may include additional regions and/or other configurations. For example, in FIG. 19C, the first region 18a and the second region 18b may each fill up one-half of the via 18. As shown, for example in FIGS. 19D and 20, the via 18 may contain more than one regions having the same material. In some embodiments, some of the vias 18 may be filled with an optically transmissive material as previously discussed, while other vias 18 may be filled with an electrically conductive material as previously discussed.

Figure 20:
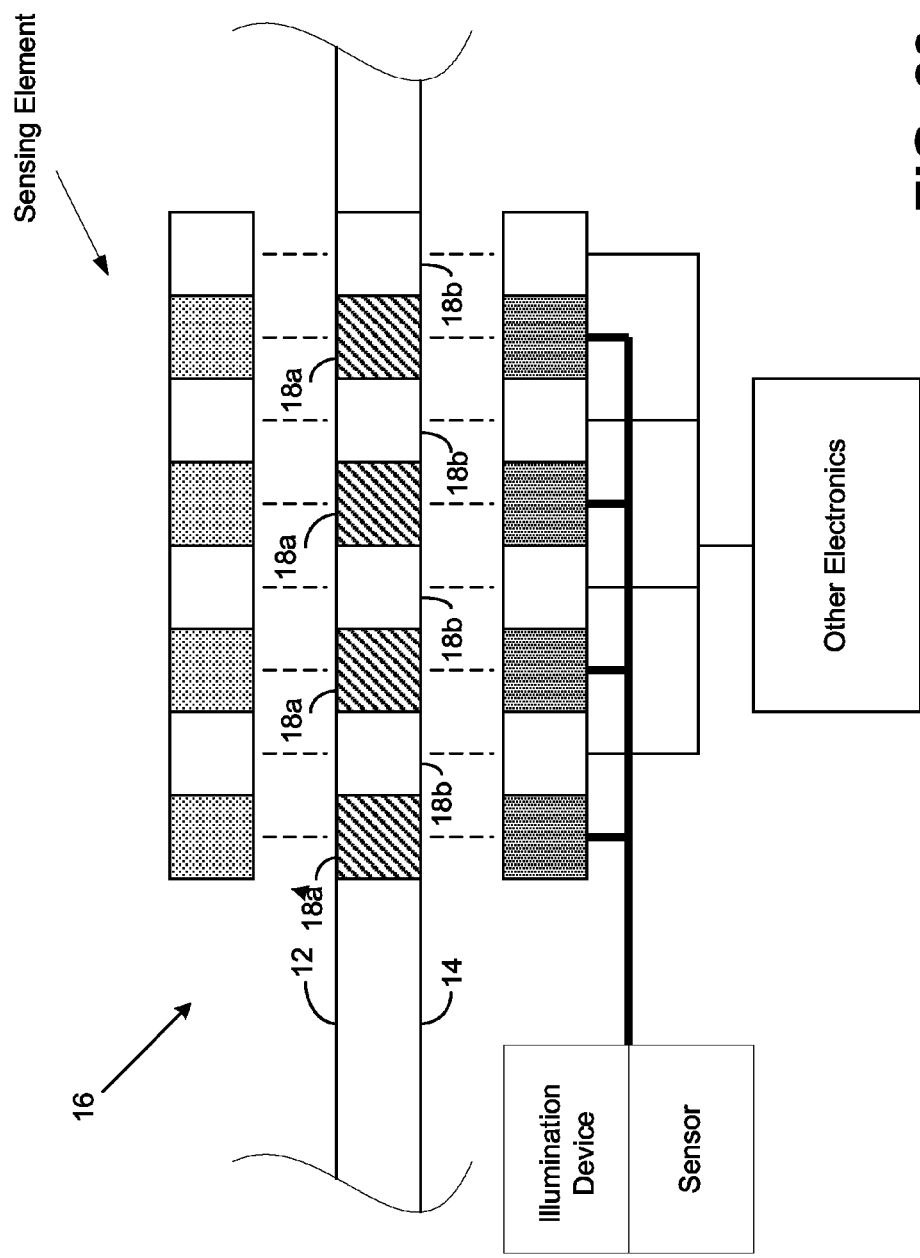
FIG. 20 is a cut-away view of a substrate with a filled via and associated electronics according to an embodiment of the present invention.

FIG. 20 illustrates a substrate 16 having a via 18 containing multiple first regions 18a and second regions 18b. One or more of the first regions 18a, which contain optically transmissive material, may be aligned with one or more of the illumination device and the sensor on the electronics side 14 of the substrate 16. One or more of the second regions 18b, which contain electrically conductive material, may be aligned with various other electronics, for example as described in the disclosure on the electronics side 14 of the substrate 16. Portions of the sensing element associated with the illumination device and/or the sensor may be aligned with one or more of the first regions 18a on the sensing element side 12 of the substrate 16. Portions of the sensing element associated with the other electronics may be aligned with one or more of the second regions 18b on the sensing element side 12 of the substrate 16.

Embodiments in which an optically transmissive material and an electrically conductive material are used to fill some or all vias may be used, for example (but not limited to), for electro-chemical, fluoresco-chemical, spectro-electro-chemical analysis and the like. In some embodiments, the electrical analysis (e.g., through the electrically conductive material) may be done simultaneously with the optical analysis (e.g., through the optically transmissive material). In other embodiments, the electrical analysis (e.g., through the electrically conductive material) may be done at a different time than the optical analysis (e.g., through the optically transmissive material). Embodiments in which multiple analyses are performed (e.g., electrical and chemical) may allow for sensing one or more parameters from multiple locations and/or for sensing one or more characteristics (e.g., an electrical signal and a fluorescence) from a particular region or sample. These one more characteristics, for example, may be processed to determine data (or more accurate data) than otherwise possible when sensing one characteristic.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A sensing apparatus comprising:
   a planar substrate having a first side and a second side that is opposite and parallel to said first side, wherein the substrate defines therethrough a via, said via being a pathway that extends from said first side to said second side of the substrate;
   a sensing element disposed on said first side, wherein the sensing element is configured to sense an analyte; and
   electronics disposed on said second side, wherein the electronics include an illumination device for illuminating the analyte,
   wherein the via is hermetically sealed from the first side of the substrate to the second side of the substrate, wherein the via is at least partially filled with an optically transmissive material, and wherein the via is at least partially filled with an additional material, said additional material comprising an electrically conductive material other than air.

2. The sensing apparatus of claim 1, wherein the optically transmissive material comprises a fritted glass material.

3. The sensing apparatus of claim 2, wherein the flitted glass material comprises at least one of quartz and silica.

4. The sensing apparatus of claim 1, wherein the optically transmissive material is concentrically arranged with respect to the electrically conductive material.

5. The sensing apparatus of claim 1, wherein the electrically conductive material comprises a fritless ink.

6. The sensing apparatus of claim 1, wherein the electrically conductive material comprises an indium tin oxide.

7. The sensing apparatus of claim 1, wherein the substrate is made of a material comprising ceramic.

8. The sensing apparatus of claim 1, wherein the substrate defines therethrough a plurality of separate vias, each of said plurality of vias being a pathway that extends from said first side to said second side of the substrate.

9. The sensing apparatus of claim 8,
   wherein at least one of the plurality of vias is at least partially filled with an optically transmissive material; and
   wherein at least one other of the plurality of vias is at least partially filled with an additional material, said additional material comprising an electrically conductive material other than air.

10. The sensing apparatus of claim 1, wherein the substrate is annealed.

11. The sensing apparatus of claim 9, wherein each via that is at least partially filled with the optically transmissive material is polished.

12. The sensing apparatus of claim 1, wherein the sensing element senses a fluorescence resonance energy transfer of the analyte.

13. The sensing apparatus of claim 1, wherein the illumination device comprises at least one of a light emitting device, a vertical cavity surface emitting laser, and an edge emitting laser.

14. The sensing apparatus of claim 1, wherein the illumination device is arranged to illuminate the analyte through the via in the substrate.

15. The sensing apparatus of claim 1, the electronics comprising a sensor for measuring a returned fluorescence from the sensing element.

16. The sensing apparatus of claim 15, wherein the sensor is arranged to sense the returned fluorescence from the sensing element through the via in the substrate.

17. A method of manufacturing a sensing apparatus, the method comprising:
   providing a planar substrate having a first side and a second side that is opposite and parallel to said first side;
   forming at least one via through the substrate, wherein said at least one via is a pathway that extends from the first side of the substrate to the second side of the substrate;
   filling the at least one via at least partially with an optically transmissive material and at least partially with an additional material, said additional material comprising an electrically conductive material other than air, such that the at least one via is hermetically sealed from the first side of the substrate to the second side of the substrate;

arranging on said first side of the substrate a sensing element configured to sense an analyte; and arranging electronics on said second side of the substrate, said electronics including an illumination device.

18. The method of claim 17, wherein the illumination device is an optical emitting device to pass light through the at least one via to the first side of the substrate, the method further comprising:

arranging a receiving device on the second side of the substrate; and arranging an optically detectable material that is reactive in an optically detectable manner on the first side of the substrate to receive light from the optical emitting device and is optically detectable through the at least one via by the receiving device.

19. The method of claim 18, wherein the sensing element is disposed directly on the first side of the substrate.

20. The method of claim 19, wherein the illumination device and the receiving device are disposed directly on the second side of the substrate.

21. The method of claim 17, wherein, after forming the at least one via, the method further includes annealing the substrate.

22. The method of claim 17, wherein, after filling the at least one via, the method further includes firing the substrate so as to harden the electrically conductive material is inside said at least one via.

23. The method of claim 17, wherein said at least one via is formed so as to be perpendicular to both the first and the second sides of the substrate.

24. The sensing apparatus of claim 1, wherein the via is perpendicular to both the first and the second sides of the substrate.

25. The sensing apparatus of claim 1, wherein the sensing element is disposed directly on said first side of the substrate.

26. The sensing apparatus of claim 25, wherein the electronics are disposed directly on said second side of the substrate.

27. The sensing apparatus of claim 5, wherein the fritless ink includes at least one of a gold paste and a platinum paste.

* * * * *